(12) United States Patent
Scherr

(10) Patent No.: US 8,579,863 B2
(45) Date of Patent: Nov. 12, 2013

(54) CATHETER PATCH

(75) Inventor: George H. Scherr, Park Forest, IL (US)

(73) Assignee: B. Braun Hospicare Limited, Bethelem, PA (US)

( * ) Notice: Subject to any disclaimer, the term of this patent is extended or adjusted under 35 U.S.C. 154(b) by 1463 days.

(21) Appl. No.: 11/370,597

(22) Filed: Mar. 9, 2006

(65) Prior Publication Data

US 2007/0225652 A1  Sep. 27, 2007

(51) Int. Cl.
*A61M 5/32* (2006.01)

(52) U.S. Cl.
USPC ........................................................ 604/174

(58) Field of Classification Search
USPC ................................. 604/174–180
See application file for complete search history.

(56) References Cited

U.S. PATENT DOCUMENTS

| | | | |
|---|---|---|---|
| 3,918,446 A * | 11/1975 | Buttaravoli | .................... 604/180 |
| 4,040,427 A | 8/1977 | Winnie | |
| 4,221,215 A * | 9/1980 | Mandelbaum | ................. 604/327 |
| D265,128 S | 6/1982 | Foerster | |
| 4,579,120 A | 4/1986 | MacGregor | |
| 4,874,380 A | 10/1989 | Hesketh | |
| 4,915,694 A * | 4/1990 | Yamamoto et al. | ........... 604/180 |
| 5,232,453 A | 8/1993 | Plass et al. | |
| 5,447,492 A * | 9/1995 | Cartmell et al. | ................. 602/58 |
| 5,833,665 A | 11/1998 | Bootman et al. | |
| 5,944,696 A * | 8/1999 | Bayless et al. | ................. 604/174 |
| 6,241,715 B1 | 6/2001 | Houser et al. | |
| 6,685,681 B2 * | 2/2004 | Lockwood et al. | ........... 604/305 |
| 6,696,077 B2 | 2/2004 | Scherr | |
| D488,230 S | 4/2004 | Ignotz et al. | |

\* cited by examiner

*Primary Examiner* — Kevin C Sirmons
*Assistant Examiner* — Andrew Gilbert
(74) *Attorney, Agent, or Firm* — RatnerPrestia

(57) ABSTRACT

The present invention relates to a patch, which can be used to secure catheters, wound drainage devices, and/or drug delivery devices, when said catheter and related devices are inserted into the body. The invention also can deliver antimicrobial substances to the site of insertion of a catheter and related devices into a body as well as other medicinal factors, such as wound and tissue healing factors that may be desired to be delivered to the site of insertion.

17 Claims, 3 Drawing Sheets

Figure no. 3
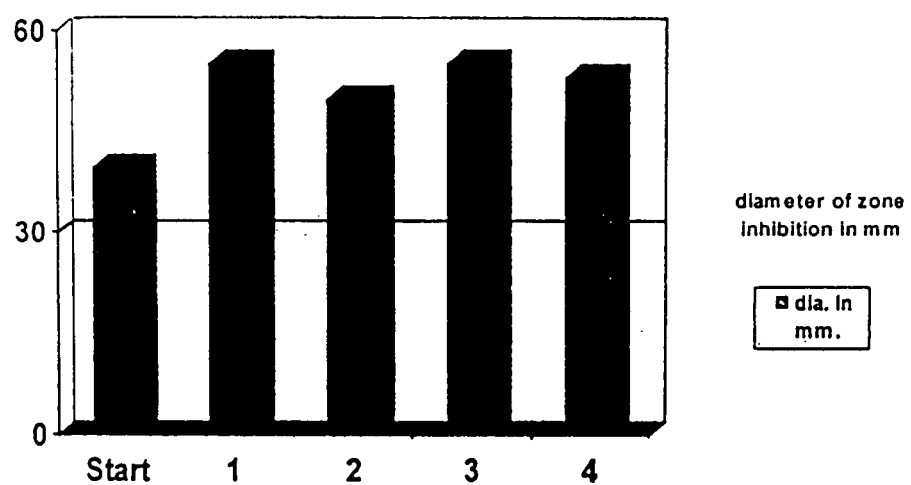
diameter of zone inhibition in mm
◘ dia. in mm.
Table no. 1
Diameter of Zone of inhibition in mm
| | |
|---|---|
| Initial | 40 |
| 1st transfer | 55 |
| 2nd transfer | 50 |
| 3rd transfer | 55 |
| 4th transfer | 53 |

CATHETER PATCH

BACKGROUND OF THE INVENTION

An examination of a catalog of a catheter manufacturing company, such as the Product Catalog of the Bard Medical Division (Bard Medical Division, 8195 Industrial Boulevard, Covington, Ga. 30014-2655) indicates the very wide array of sizes, types, as well as diameters of various catheters or drainage devices and related products that are utilized by insertion of such devices into humans or animals. Since many of the wound drainage devices and catheter devices may remain so inserted into the body for extended periods of time, it has become necessary to affix the catheter at the point of insertion in order to ensure its retention at the site of insertion and also to provide and deliver antimicrobial activity to the insertion site since the piercing of the skin frequently can result in a site of microbial entrance and infection.

A typical device that has hereto been developed for such purpose is described in U.S. Pat. No. 5,833,665 invented by Bootman et al. Because of the great variability of the diameter of various catheters and also needles that are inserted into the body to which catheters may be a part, it would be desirable that the catheter patch be prepared in a manner, which would lend itself to utilization with a relatively wide variety of diameters of catheters. This would obviate the necessity of preparing different size patches for different size catheters and related devices. It is therefore an object of the present invention, to develop a catheter patch that has an adjustable center that would fit over the catheter and that said configuration would be applicable for use for a wide variety of diameters of a catheter.

The invention of Winnie (U.S. Pat. No. 4,040,427), describes a device that is intended for use with catheters and related devices. The utility of a series of slits emanating from a small central opening in the instant application provides the versatility of the patch to be used with a wider range of diameters of catheters and related devices than could be utilized by the invention of Winnie. If larger catheters are required for different applications, Winnie's invention would mandate that a series of different size diameters as shown in FIG. 1 of Winnie's patent, labeled 32 would be necessary to accommodate different size diameters of catheters. Whereas, in the instant application, the small slits around the central opening can give way to accommodate a much wider series of diameters without having to design a different patch for each diameter. Therefore, the utility of these slits, which nowhere appear in the Winnie patent provide a utility, which also provides novelty for the instant design submitted herein.

There is another attribute of the instant application of Scherr, which is not addressed by the Winnie patent, and that concerns the utilization of a patch which when placed next to the skin of a patient into which a catheter has been inserted, that the constitution of the patch placed against the opening will have an antimicrobial activity in the event that exudate will begin to appear at the cite of injection. Such infections have been known in the past and in fact can be very dangerous. Thus chlorhexidine-impregnated patches used for similar purposes as described in the instant application have been shown to have nosocomial *Pseudomonas cepacia* infections associated with chlorhexidine contaminations (Am. J. Med.; VOL 73 ISS August 1982, P 183-186). The cycloheximide patch also had the undesirable attribute of resulting in anaphylactic reactions, (United States Food and Drug Administration, FDA Public Health Notice dated Mar. 11, 1998, entitled POTENTIAL HYPERSENSITIVITY REACTIONS TO CHLORHEXIDINE-IMPREGNATED MEDICAL DEVICES) an attribute not present in the constitution of the material from which the patches described herein are made. It is for these reasons that applicant has taken the pains to indicate the composition of the material from which the patch is prepared and the antimicrobial activity which the patch has been shown to contain. Data for this can be found in the 510(k) application with the United States Food and Drug Administration, which application (United States Food and Drug application K011618) has been approved for this composition, and which constitutes one preferred composition of the patch of the instant application.

The invention of Ignotz, et al. (U.S. Pat. No. D488,230), is an infusion adhesive patch that has three openings with an enclosed perimeter around the three openings of the patch. Consequently, the patch would have to be applied to the skin of the patient before a needle and the inclusive catheter is inserted through one of the openings of the patch. Should it happen that the veins are not readily available to the entrance of the needle and the medical attendant would have to find another site of injection into a vein, then the patch would have to be removed from the initial site and transferred to a secondary site before the insertion of a needle through one of the openings of the patch. In the instant invention of applicant, the patch permits itself to be placed over the needle and/or over entrance of the catheter after insertion of a needle attached to a catheter has been achieved (emphasis added). If it is necessary for the medical attendant to try one or two injection sites before succeeding, it is no deterrent to the patch being placed over the entrance of the catheter and adhere it to the entrance site against the skin where it can be fixed in place with adhesive. This is a significant attribute of the instant application described herein which is totally lacking in the patent of Ignotz, et al. and therefore the novelty of the instant application has no counterpart in the invention of Ignotz, et al.

The invention of Foerster (U.S. Pat. No. D265,128) describes a protective mammary bandage. The slit in this bandage permits the bandage to be formed and sealed up with a tape so that it will fit over a breast. The central opening obviously, is for the woman's nipple.

In use, the slit in the Foerster device and the hole opening in the center of the Foerster device play absolutely no role that in any way could be construed as being applicable for use with a catheter. In addition, the mammary bandage of Foerster lacks the slits that would make it feasible to fit over a woman's breast if there was consideration required for the size of the woman's nipples of the breast. The Foerster device is not amenable for use for a wider array of sizes of breast nipples or for different diameter catheters, if in fact the Foerster device were intended for and could even be used as a patch for a catheter or related device. Consequently, there is no prior art in the Foerster device that is relative to the device in the instant application.

The subject of Houser et al.'s patent, (U.S. Pat. No. 6,241, 715 B1), is also a breast pad which, similar to the Foerster mammary bandage, contains a slit leading to a central opening so that the slit can permit the form of the device to be contoured around the woman's breast leaving the central opening open for the nipple of the breast.

All of the commentary we have submitted above relative to the Foerster device is applicable to the Houser, et al. device and is repeated here by reference.

The device of Plass et al. (U.S. Pat. No. 5,232,453), essentially is very much similar to the device of Winnie (U.S. Pat. No. 4,040,427) except that the former has the proviso of providing adhesive strips, which may be attached to a catheter, that is passed through the opening of the device of Plass et al. as illustrated by the opening of number 42 in FIG. 3 of Plass et al's patent. Otherwise, the central opening in the Plass et al. patent number 42 is fixed as occurs in the patent of Winnie. The slit labeled number 46 in FIG. 3 of the device of Plass et al. is essentially the slit of Winnie's device except that the slit is in the form of a narrow angular quadrant labeled number 28 in FIG. 1 of the Winnie patent.

The Plass et al. patent will accommodate a diameter of a catheter depending upon the diameter of the opening in the center of the catheter holder and Plass et al. recognizes this restraint in that he sets forth in his patent that:

"The hole 42 may be about 7.5 mm in diameter, or such other value as may accommodate the required catheter, . . . ."

Obviously, for each different size of diameter of a catheter to be utilized, the Plass et al. patent would have to manufacture a device having a different diameter opening to accommodate the catheter, a totally unnecessary attribute that our invention circumvents by placing a number of slits emanating from the central opening of the catheter patch in our instant device.

The patent of Hesketh (U.S. Pat. No. 4,874,380), provides a central opening (Number 12 in FIG. 4 of Hesketh's patent) which is overly large. Hesketh, himself, indicates that the opening is such that it can accommodate catheters of an outside diameter from 2 mm to 10 mm:

"With this arrangement, irrespective of whether a catheter of outside diameter 10 mm or more, or a small catheter of outside diameter of 2 or 3 mm is employed, one can achieve a satisfactory clamping of the catheter without an undesired deformation of its wall and occlusion of its internal passage."

In order that the catheter, which is illustrated in FIG. 4 by the number 34, is affixed and will not move around, Hesketh has designed a locking mechanism (Item 22 in his FIG. 4) which locking mechanism will lock the catheter in place to the dressing and is composed of a ratchet and locking mechanism, which is adjusted depending upon the diameter of the catheter that is used. By this devise, relatively small catheters as is demonstrated in Hesketh's FIG. 4, still leave an opening (Number 12 in FIG. 4) which is open to the outside and does not represent a closed dressing in the area of the entrance to the body.

Consequently, the mechanism that Hesketh uses is in contrast to the multiple slit mechanism of the instant patent of Scherr in which the slits emanating from the central portion of the catheter patch permit a relatively wide array of diameters to be inserted through the patch without leaving a clear opening which is exposed to air, so exposing the entrance into the body to possible outside contamination.

Further, in order for the Hesketh device to maintain a fixed catheter it is necessary for the ratchet device to be attached to a component labeled Number 10 in FIG. 4, which is then separately adhered to the basic patch labeled Number 14 in FIG. 4 of the Hesketh patent. Consequently, there is little relationship between the basic novelty inherent in the Hesketh patent and that of the instant application of Scherr.

The U.S. Pat. No. 4,579,120 of MacGregor shows a slit emanating from the outside of the device to the central portion of the device as shown in FIG. 4 in the MacGregor patent, but there are no slits as is shown in FIGS. 1 and 2 of the MacGregor device to compensate for differences in diameter of a catheter as shown in the instant application. The passage 26 as shown in FIGS. 2 and 4, utilizes a cross section which is equal to the diameter of whatever electrical lead or catheter is inserted through the opening number 26, as is clearly set forth by MacGregor in his specification:

"With the exception of the flare 28, the passage 26 is of substantially constant cross-section over its length. The cross-sectional shape of the passage is substantially identical to the cross-sectional shape of the lead L and the diameter of the passage 26 is sized so that it snugly fits the lead L when the lead is inserted through the passage as shown in FIG. 1."

Even in the device as illustrated in FIG. 4 of the MacGregor patent, the slit makes it possible to insert the device over a protruding lead from the body, which lead is then moved into the passage 26 and whatever lead is protruding from the passage 26, as shown in FIG. 4 of the MacGregor patent, the portion 22 is then tied tightly to ensure that the lead (L) snugly fits into the passage 26. Thus, MacGregor points out that:

"Once the lead has been positioned, the other end of the lead outside of the body is inserted upwardly through the passage 26 via needle N and the disc 10 is slid downwardly along the lead until it contacts the skin of the patient and conforms to the curvature of the patient's skin surface at the exit location. At this point, the disc 10 and its surface 12 are adhered to the body at the lead exit location with the adhesive layer 14 to anchor the disc 10 and the lead L firmly to the body. The lead L, which is also of substantially constant cross-section over its length, fits snugly in the passage 26.

The lead is preferably further secured by tying or binding with a suitable thread-like member, such as a suture 30, about the stem portion 22 of the bulbous shaped head 20, as shown in FIG. 1. Tying with the suture 30 not only seals the passage 26 against the entry of contaminants to protect against infection, but also firmly secures the lead L in the passage 26 against sliding or other displacement. Although a suture 30 is shown about the stem portion 22, it will be understood that other forms of fixation may be employed, such as a clamp, clip, applied adhesive, elastic band, etc."

Consequently, each device of MacGregor has to be manufactured separately to accommodate the specific diameter of an electric lead or catheter that is either emanating from the body of a patient or is to be inserted into the body of a patient; unlike the latitude provided in the instant device of Scherr, in which one device with a series of slits emanating from a central opening permits a rather wide latitude of cross-sectional diameters to be inserted therein.

Because many catheters may be inserted into an appropriate part of the body and remain there for extended periods of time, it would be desirable that the site of insertion of any needle or similar device penetrating the body, be maintained in an environment that enhances antimicrobial activity to avoid bacterial contamination at that site. It is therefore one object of the invention that it would lend itself to being die cut or punched from a variety of prepared sheets that would contain antimicrobial activity for extended periods of time.

Since the maintenance of an inserted catheter may result in some tissue exudate being released from the site of the wound where the catheter enters the body, the catheter patch so utilized would benefit from having the capability to absorb such exudate. It is therefore another object of the instant invention of the catheter patch that would lend itself to being punched or die cut from various compositions and retain a significant level of absorption of any exudate that is released at the site of insertion of the catheter.

BRIEF DESCRIPTION OF THE FIGURES

FIG. 3: A graph showing the relatively uniform antimicrobial inhibition of the preferred embodiment of the catheter securing device over a period of 4 serial transfers
TABLE 1 shows the quantitative zones of inhibition of the preferred composition of the antimicrobial surface of the catheter securing device described herein.

DESCRIPTION OF THE PREFERRED EMBODIMENTS

Figure 1:
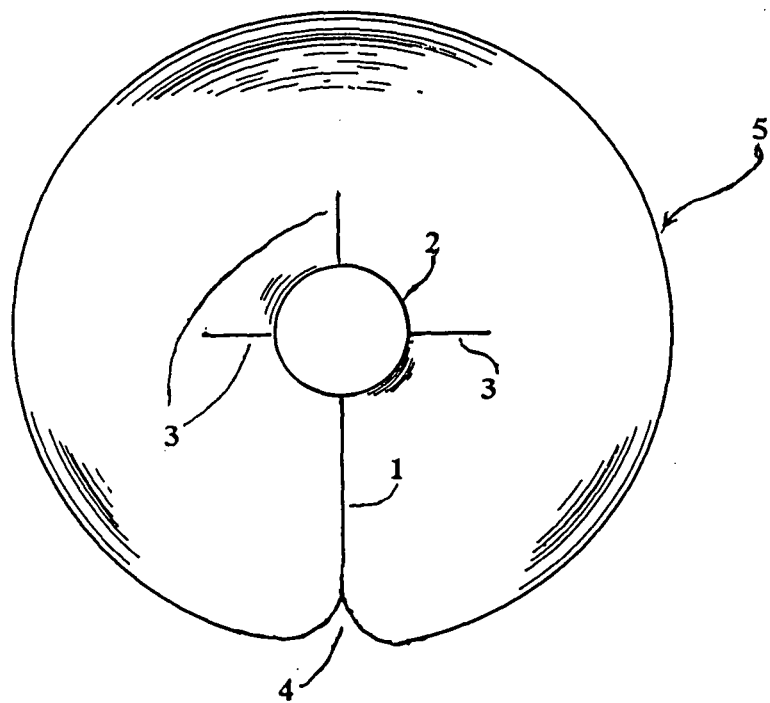
FIG. 1: A plan view of the catheter securing device

The face or plan view of the patch is depicted in FIG. 1. The catheter-securing patch as depicted in FIG. 1 may be punched or die cut from sheets of silver alginate such as those prepared and described in U.S. Pat. No. 6,696,077 B2 issued Feb. 24, 2004; the contents of said U.S. patent are cited herein and made a part of this application in its entirety. In such an embodiment, the patch is cut in a circular form (FIG. 1) and a slit (FIG. 1-No. 1) which extends from the edge of the patch to the center of a hole cut in the patch (FIG. 1-No. 2) provides the insertion site of the patch over a catheter. The "v" shaped opening (No. 4 in FIG. 1) is provided as convenience for the patch to slip over the catheter as the catheter is pushed up the slit to the central point, which contains a central circular opening (No. 2) from which opening, 3 additional slits emanate (FIG. 1-No. 3). The total of four slits—for the central hole (No. 2) act as a compensatory mechanism for accommodating different diameters of patches, which slits will significantly reduce the distortion of the patch if the diameter of the catheter is greater than the diameter of the opening (No. 2) in the center of the patch.

Figure 2:
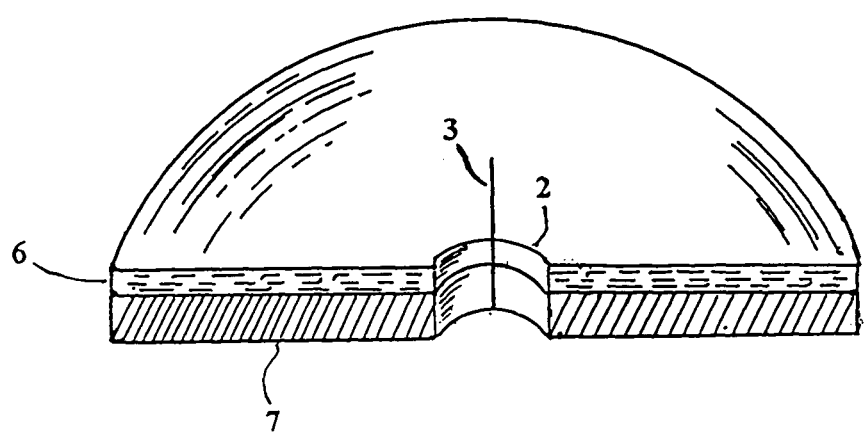
FIG. 2: A cross-section perspective view of the catheter securing device

An examination of the antimicrobial activity of one embodiment of the patch as shown in FIG. 1, when die cut from a sheet containing silver alginate, the preparation of which is described in U.S. Pat. No. 6,696,077 B2 is depicted in FIG. 2. FIG. 2 is a cross section planar view of the patch in which 2 shows the center opening of the patch, 3 shows one of the slits emanating from the center hole of the patch, 6 shows the silver alginate layer of the patch, and 7 shows a polyurethane backing of the patch onto which the silver alginate layer has been affixed.

The silver alginate patch as depicted in FIGS. 1 and 2 has the advantage in that the antimicrobial activity of the silver alginate surface has been demonstrated to be active over extended periods of time as demonstrated in Example 1, FIG. 3, and Table 1.

EXAMPLE 1

A square inch of silver alginate foam dressing was checked for reusability against *Ps. Aeruginosa*. Nutrient agar in which, the agar content was increased to 10% was inoculated with 0.1 ml of actively growing culture and surface spread. Hard agar was used to prevent too rapid water uptake from the gel. The silver alginate specimen was placed on the agar surface and diffusion was allowed to commerce for 3 hours under refrigeration. The plate was then incubated at 35° C. for 16 hours. The zone of inhibition in mm was measured and the test specimen was then transferred to another inoculated agar plate. This process was repeated 5 times. The results are presented in Figure No. 3 and Table 1.

From the forgoing it will be seen that the invention described herein results in several advantages not present in prior methods for utilizing catheters and related devices, which devices may be subject to tissue exudates as well as potential infectious organisms at the site of entrance into the body. Although a preferred embodiment of a composition described herein utilizes a silver alginate foam product with a backing of polyurethane, the latter of which would have a capacity for absorption of exudate in excess of 25 times the weight of the patch, backings other than polyurethane are amenable for utilization from which the catheter patch may be die-cut or punched. Thus, for example, if the catheter is to be inserted for a relatively short period which might reduce significantly the amount of exudate that might require absorption, the catheter patch may be die cut from a composition with a backing of cotton or polyester which would have the capability to absorb exudate far less than a polyurethane foam backing.

The slit 2 makes it feasible to insert the patch over the insertion tube after the catheter has been inserted into a patient. For catheter patches that do not have this unique attribute, but are affixed to the patient's body prior to the insertion of the catheter into the body, a failure of a catheter needle to be inserted in an area that is desirable would then require that the catheter patch be removed and transferred to another site, an additional procedure of this kind being unnecessary with the invention set forth herein.

Compositions other than silver alginate foam dressings are amenable for utilization from which the catheter patch may be die-cut or punched. Thus, compositions other than that of silver alginate may be utilized as antimicrobial agents such as antibiotics, without deviating from the essential attributes of the invention described herein.

A desirable size of a catheter patch as it is illustrated in FIG. 1 would be one that has a cross-section diameter of 1 inch, although patches of other sizes having the same attributes as described herein can be utilized without deviating from the basic tenets of the invention described herein. Although the configuration shown in FIG. 1 is circular, it is clear that other geometrical shapes may be utilized without deviating from the essential attributes that are novel to the invention described herein.

Should it be desirable to utilize such patches for catheters, delivery tubes, or wound drainage tubes that may be of a relatively large size, it is clear that the cross-section diameter of the central aperture (No. 2) can be increased accordingly and the number of slits as shown in FIG. 1-No. 3) may be increased without deviating from the essential novel attributes of the invention described herein.

It will be understood that the embodiments of the present invention, which have been described, are merely illustrative of a few of the applications of the principles of the present invention. Numerous modifications may be made by those skilled in the art without departing from the scope of the invention described herein.

REFERENCES CITED

Bard Medical Division, 8195 Industrial Boulevard, Covington, GA 30014-2655
Am. J. Med.; VOL 73 ISS Aug 1982, P183-186
United States Food and Drug Administration, FDA Public Health Notice dated Mar. 11, 1998, entitled POTENTIAL HYPERSENSITIVITY REACTIONS TO CHLORHEXIDINE-IMPREGNATED MEDICAL DEVICES
The following patents are cited.
Bootman et al.—U.S. Pat. No. 5,833,665
Winnie—U.S. Pat. No. 4,040,427
Ignotz et al.—U.S. Pat. No. D488,230
Foerster—U.S. Pat. No. D265,128
Houser et al.—U.S. Pat. No. 6,241,715 B1

Hesketh—U.S. Pat. No. 4,874,380
MacGregor—U.S. Pat. No. 4,579,120
Scherr—U.S. Pat. No. 6,696,077 B2

I claim:

1. A device to be used to secure catheters, wound drainage devices, and/or drug delivery devices, when said catheter or related devices are inserted into the body, the device comprising a patch defining an outer edge and a central hole, wherein an entrance slit extends through the patch from the outer edge of the patch to the central hole in the patch, and wherein at least one additional slit extending through the patch emanates from the central hole, the entrance slit and the at least one additional slit are configured as narrow passages such that a clear opening is not defined between portions of the patch adjacent to the respective slit.

2. The device of claim 1 wherein said additional slits extending through the patch and emanating from said central hole are not less than two in number.

3. The device of claim 1 wherein at least one surface of the patch contains an antimicrobial agent.

4. The device of claim 1 wherein a backing of the patch contains an exudate-absorbing member.

5. The device of claim 3 wherein said antimicrobial agent is a composition of silver.

6. The device of claim 1 wherein said patch is generally disc-shaped.

7. The device of claim 1 wherein the entrance slit is beveled along the outer edge.

8. A device for securing a catheter, a wound drainage device, and/or a drug delivery device inserted into a body, the device comprising: a patch defining an outer edge and a through hole, with an entrance slit extending through the patch from the outer edge of the patch to the through hole, and at least one additional slit extending through the patch emanating from the central hole such that the patch is divided into at least two portions about the through hole, each portion having an inner edge defining a portion of a through hole perimeter, and wherein the entrance slit and the at least one additional slit are configured as narrow passages such that a clear opening is not defined between portions of the patch adjacent to the respective slit.

9. The device of claim 8 wherein the at least two portions are moveable relative to one another such that a diameter of the through hole perimeter is adjustable.

10. The device of claim 8 wherein said additional slits extending through the patch and emanating from said central hole are not less than two in number and the portions about the through hole are at least three in number.

11. The device of claim 8 wherein said additional slits extending through the patch and emanating from said central hole are not less than three in number and the portions about the through hole are at least four in number.

12. The device of claim 8 wherein said additional slits extend less than to the outer edge of the patch.

13. The device of claim 8 wherein at least one surface of the patch contains an antimicrobial agent.

14. The device of claim 13 wherein said antimicrobial agent is a composition of silver.

15. The device of claim 8 wherein a backing of the patch contains an exudate-absorbing member.

16. The device of claim 8 wherein said patch is generally disc-shaped.

17. The device of claim 8 wherein the entrance slit is beveled along the outer edge.

* * * * *